United States Patent [19]

Hunter et al.

[11] 4,142,886

[45] Mar. 6, 1979

[54] SUBSTITUTED BENZIMIDAZOLE COMPOUNDS AND USE AS HERBICIDES

[75] Inventors: Don L. Hunter, Anaheim, Calif.; Wayne S. Belles, Moscow, Id.

[73] Assignee: United States Borax & Chemical Corporation, Los Angeles, Calif.

[21] Appl. No.: 807,592

[22] Filed: Jun. 17, 1977

[51] Int. Cl.² ................ A01N 9/22; C07D 235/08
[52] U.S. Cl. .................................. 71/92; 548/325; 548/329
[58] Field of Search .............. 548/325, 329; 71/92

[56] References Cited

U.S. PATENT DOCUMENTS

| | | | |
|---|---|---|---|
| 3,317,554 | 5/1967 | Goldsmith et al. | 548/325 |
| 3,325,271 | 6/1967 | Goldsmith et al. | 548/325 |
| 4,074,046 | 2/1978 | Mohan | 548/325 |

FOREIGN PATENT DOCUMENTS

| | | | |
|---|---|---|---|
| 2625839 | 12/1976 | Fed. Rep. of Germany | 548/325 |
| 1155336 | 12/1968 | France | 548/329 |
| 1015937 | 1/1966 | United Kingdom | 548/325 |

OTHER PUBLICATIONS

Itaya, Yakugaku Zasshi 82, pp. 1–5, (1962).

*Primary Examiner*—Natalie Trousof
*Assistant Examiner*—Natalia Harkaway
*Attorney, Agent, or Firm*—James R. Thorton

[57] ABSTRACT

1,2-Di-lower alkyl-5-branched chain alkyl benzimidazoles and their use as selective herbicides.

14 Claims, No Drawings

SUBSTITUTED BENZIMIDAZOLE COMPOUNDS AND USE AS HERBICIDES

This invention relates to a novel class of substituted benzimidazoles and to their use as selective herbicides.

BACKGROUND OF THE INVENTION

Various substituted benzimidazoles are known to be useful as herbicides. U.S. Pat. 3,325,271 describes the use of a broad class of substituted benzimidazoles as herbicides in which there is at least one substituent on the aromatic ring or at the 1 or 2 position of the molecule. The 1 and 2-substituents may be alkyl, and the aromatic substituents are selected from nitro, halo, lower alkyl, lower alkoxy and halo-lower alkyl. Other patents relate to specific benzimidazole compounds, especially those having at least one trifluoromethyl substituent, either on the aromatic ring or at the 2-position. Motoichi Itaya, Yakagaku Zasshi, Volume 82, pages 1–5 (1962) describes the synthesis of certain 5(6)-substituted 2-methylbenzimidazoles in which the 5(6)-substituent may be a branched chain alkyl group such as isopropyl, tert-butyl, and isoamyl (see Chem. Abstracts, Volume 57,9840).

This invention relates to a class of specific 1,2,5-substituted benzimidazoles which are useful as selective herbicides. The compounds of this invention possess improved selective herbicidal properties over the closest related compounds of Itaya, especially when used as a pre-emergence treatment.

According to the present invention, there are provided benzimidazole compounds of the formula:

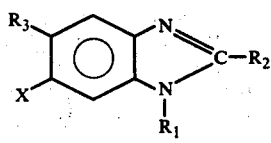

in which each of $R_1$ and $R_2$ are alkyl of 1 to 3 carbon atoms, $R_3$ is a branched chain alkyl group of 3 to about 6 carbon atoms, and X represents hydrogen or halogen, especially bromine and chlorine. Also provided are the N-oxide derivatives thereof. Thus, the groups represented by $R_1$ and $R_2$ may be methyl, ethyl, n-propyl or isopropyl; preferably $R_1$ and $R_2$ are methyl. The branched chain alkyl groups represented by $R_3$ may be isopropyl, tert-butyl, sec-butyl, tert-pentyl, cyclopropyl, and the like. Preferably, $R_3$ is isopropyl or tert-butyl, and X represents hydrogen.

The compounds of this invention are generally crystalline solids or oils which are soluble in many common organic solvents such as ethanol, benzene, n-hexane, etc. They will form salts with mineral acids such as hydrochloric acid and some organic acids, such as trifluoroacetic acid, and such salts are generally soluble in water. The compounds may be readily prepared by several procedures such as by reaction of the corresponding ortho-phenylenediamine with an alkanecarboxylic acid or carboximidate. The various intermediates are prepared by synthetic procedures well-known to the organic chemical art. A typical reaction scheme is illustrated below, in which $R_1$, $R_2$, $R_3$ and X have the significance previously assigned.

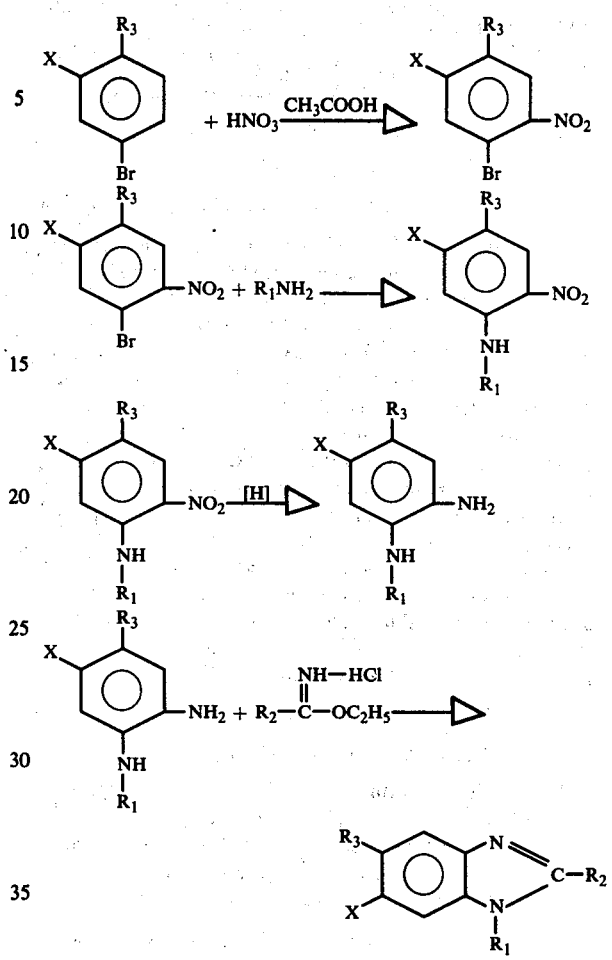

The benzimidazole-forming reaction employs the carboximidate, generally in its hydrochloride form. When an alkanecarboxylic acid is used to form the benzimidazole, the reaction takes place in the presence of a mineral acid. The desired products are isolated from the reaction mixtures and purified by conventional procedures.

The N-oxide derivatives are prepared by the catalytic reductive cyclization of the corresponding 2-nitroacylanilide, such as by hydrogenation over palladium catalyst. The reaction can be illustrated as follows:

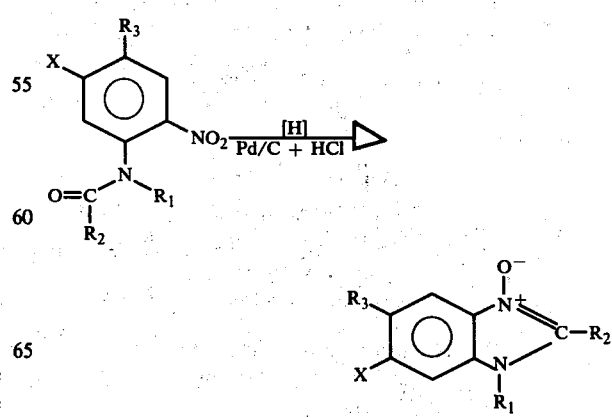

A small amount of the corresponding o-phenylenediamine is also formed in the reaction, but may be separated by taking advantage of differences in solubility of the products in hydrocarbon solvents.

The following examples illustrate the preparation of representative compounds of this invention.

Example I

1,2-dimethyl-5-isopropylbenzimidazole

A mixture of 6.66 g. (0.041 mole) of $N^2$-methyl-5-isopropyl-1,2-phenylenediamine and 10.02 g. (0.081 mole) of ethyl methylcarboximidate hydrochloride in 100 ml. of absolute ethanol was stirred at room temperature for 40 hours and then refluxed for 18 hours. The reaction mixture was distilled to dryness under reduced pressure, 100 ml. of 4N HCl was added to the residue and then the mixture refluxed for 22 hours. After cooling, the resultant mixture was filtered and the filtrate added dropwise to 200 ml. of stirred ice and water containing 50 ml. of conc. ammonium hydroxide. The precipitated product was isolated by filtration, washed with water and then air-dried. The crude product was dissolved in 75 ml. of refluxing cyclohexane, filtered and the filtrate allowed to cool. The desired product crystallized from the cooled cyclohexane and was removed by filtration to give 2.73 g. (35.8%), melting at 130°–131° C.

Example II

1,2-dimethyl-5-tert-butylbenzimidazole

The desired product was obtained by reaction of $N^2$-methyl-5-tert-butyl-1,2-phenylenediamine with ethyl methylcarboximidate hydrochloride according to the procedure of Example I. The crystalline product (4.17 g.) (55.3%) melts at 137.5°–138.5° C.

Example III

1,2-dimethyl-5-isopropylbenzimidazole N-oxide

A mixture of 3.2 g. (14 mmoles) of N-methyl-4-isopropyl-2-nitroacetanilide, 0.5 g. of 10% Pd on carbon, 4.9 ml. of conc. HCl and 70 ml. of absolute ethanol was hydrogenated at an initial pressure of 31 psi. for 3 hours. After filtering through Celite, the filtrate was evaporated under reduced pressure to about 5 ml. To the residue was added 20 ml. of water and the pH adjusted to 8 with sodium carbonate. The solution was then extracted twice with 80 ml. of methylene chloride, the combined extracts were dried over anhydrous sodium sulfate and evaporated under reduced pressure to dryness. The residue was passed through a silica gel column with a mixture of 98.5% methylene chloride and 1.5% methanol as eluant. The first fraction contained $N^1$-acetyl-$N^1$-methyl-3-isopropyl-1,2-phenylenediamine (about 0.2 g.). The eluant was changed to 88% n-hexane and 12% methanol to give the desired N-oxide as the hydrate (2.9 g.), m.p. 94°–97° C.

Examples IV–XVII

The following are examples of other representative compounds according to this invention which may be prepared by the procedures described above.

IV. 1-ethyl-2-methyl-5-tert-butylbenzimidazole, m.p. 133°–134° C.

V. 1,5-diisopropyl-2-methylbenzimidazole, oil

VI. 1-isopropyl-2-methyl-5-tert-butylbenzimidazole, m.p. 147°–149° C.

VII. 1-ethyl-2-methyl-5-isopropylbenzimidazole, oil

VIII. 1-ethyl-2-methyl-5-isopropyl-6-chlorobenzimidazole, m.p. 115.5°–116.5° C.

IX. 1,5-diisopropyl-2-methyl-6-chlorobenzimidazole, m.p. 100.5°–101.5° C.

X. 1,2-dimethyl-5-isopropyl-6-chlorobenzimidazole, m.p. 145.5°–146.5° C.

XI. 1,2-dimethyl-5-tert-pentylbenzimidazole, m.p. 129°–132° C.

XII. 1-n-propyl-2-methyl-5-isopropylbenzimidazole

XIII. 1-methyl-2-ethyl-5-tert-butylbenzimidazole

XIV. 1,2-dimethyl-5-cyclopropylbenzimidazole

XV. 1,2-dimethyl-5-isopropyl-6-bromobenzimidazole

XVI. 1,2-dimethyl-5-tert-butylbenzimidazole N-oxide

XVII. 1-methyl-2-ethyl-5-sec-butylbenzimidazole N-oxide

Examples XVIII–XIX

The hydrochloride salts may be prepared by dissolving the benzimidazoles in methanol containing hydrogen chloride (about 15%). Removal of the solvent and excess HCl by evaporation under reduced pressure gives the crystalline HCl salt.

XVIII. 1,2-dimethyl-5-isopropylbenzimidazole hydrogen chloride, m.p. 63° C.

XIX. 1,2-dimethyl-5-tert-butylbenzimidazole hydrogen chloride, m.p. 262°–265° C.

The compounds of this invention are useful as selective herbicides for controlling weeds in crops. They can be applied as either a pre-emergence or a post-emergence treatment; that is, they can be applied to soil in which the weeds will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds may be applied to the soil surface prior to emergence of the weeds or may be incorporated, such as by mixing into the top 1 to 3 inches of the soil prior to planting the crop. When used as a post-emergence treatment, it is preferred that a directed spray be employed, thereby directing the application of the herbicide onto the foliage of the weeds and away from the foliage of the desirable crop plants. Weeds, as used herein, is meant to include any plant growth which is undesirable.

The compounds are especially useful for selectively controlling weeds in the presence of desirable crops such as peanuts, corn, rice, wheat and, when applied pre-emergence, cotton. The weeds controlled include many of the broadleaf and grassy weeds such as lambsquarter, mustard, pigweed, velvetleaf, cocklebur, prickly sida, foxtail, jimsonweed, wild oats, and barnyardgrass.

Generally, an application rate of from about 0.25 to about 10 pounds of one or more of the active compounds per acre is effective in controlling weed growth. Preferably, an application rate in the range of about 0.75 to 5 pounds per acre is employed pre-emergence, and from about 0.5 to 2 pounds per acre post-emergence is employed.

The following examples illustrate the herbicidal activity of representative compounds of this invention.

Example XX

The compounds to be tested were evaluated as both a pre-emergence and post-emergence treatment. Greenhouse flats were planted to soybeans (SB), velvetleaf (VL), oats (O) and millet (M). The flats were sprayed on the same day as planting with an ethanol solution (sometimes containing added dioxane) of the compound to be tested at a rate of 5 pounds per acre. Another set of flats with the same plants was treated after the plants had emerged and were about one inch in height. These flats were also sprayed with the solution of the compound to be tested at a rate of 5 pounds per acre. The flats were kept in the greenhouse and watered when needed. Twenty-one days after treatment, the flats were examined and the plants rated for herbicidal activity on a 0–9 scale in which 0 = no effect
1 = <10% injury
2 = 10–40% injury
3 = 40–70% injury
4 = >70% injury
5 = <25% kill
6 = 25–50% kill
7 = 50–75% kill
8 = 75–99% kill
9 = 100% kill The results are given in Table I.

TABLE I

| compd. No. | Herbicidal Activity | | | | | | | |
|---|---|---|---|---|---|---|---|---|
| | Pre | | | | Post | | | |
| | SB | VL | O | M | SB | VL | O | M |
| I | 9 | 9 | 9 | 9 | 9 | 9 | 9 | 9 |
| II | 9 | 9 | 5 | 8 | 9 | 9 | 9 | 9 |
| III | 3 | 8 | 2 | 2 | 8 | 9 | 6 | 9 |
| IV | 2 | 9 | 5 | 6 | 7 | 9 | 7 | 9 |
| V | 1 | 9 | 1 | 0 | 5 | 9 | 5 | 8 |
| VI | 0 | 8 | 0 | 0 | 3 | 9 | 0 | 6 |
| VII | 9 | 9 | 8 | 9 | 7 | 9 | 9 | 9 |
| VIII | 2 | 9 | 5 | 9 | 9 | 9 | 8 | 9 |
| IX | 4 | 1 | 0 | 9 | 7 | 9 | 1 | 9 |
| X | 3 | 9 | 6 | 9 | 9 | 9 | 9 | 9 |
| XI | 9 | 9 | 2 | 8 | 9 | 9 | 8 | 9 |
| XVIII | 4 | 9 | 5 | 9 | 9 | 9 | 9 | 9 |
| XIX | 4 | 9 | 3 | 9 | 9 | 9 | 9 | 9 |

Example XXI

Several compounds were evaluated as post-emergence herbicides in greenhouse tests with a broad group of crops and weeds. The compounds were applied at a rate of 1 pound per acre to the plants when they were about one inch in height. Twenty-one days after treatment, the plants were rated on the 0 to 9 scale described in Example XX. Where two numbers are used, i.e. 8/4, the first number represents the percent kill and the second number is the injury to the remaining plants. The results are given in Table II and are an average of two replicates.

TABLE II

| Plant Species | Activity - Post | | | |
|---|---|---|---|---|
| | Compd. IV | Compd. V | Compd. VI | Compd. VII |
| alfalfa | 9 | 9 | 8/4 | 9 |
| corn | 0 | 0 | 0 | 0 |
| cotton | 8/3 | 5/3 | 0/3 | 7/2 |
| dry beans | 9 | 0/3 | 0/3 | 8/4 |
| peanuts | 0/1 | 0/2 | 0 | 0/2 |
| rice | — | 0 | 0 | 0/1 |
| soybeans | 0/2 | 0/2 | 0/2 | 5/4 |
| wheat | 0/2 | 0 | 0 | 0/1 |
| cocklebur | 9 | 0/2 | 0/3 | 7/3 |
| Jimsonweed | 9 | 8/4 | 9 | 8/4 |
| lambsquarters | 9 | 8/3 | 6/2 | 9 |
| morningglory | 0/3 | 0/3 | 0/2 | 5/3 |
| mustard | 9 | 9 | 8/3 | 9 |
| prickly sida | 7/2 | 5/2 | 6/2 | 8/4 |
| pigweed | 9 | 6/3 | 7/2 | 9 |
| sesbania | 6/3 | 5/3 | 5/2 | 8/4 |
| velvetleaf | 9 | 8/3 | 8/4 | 9 |
| barnyardgrass | 0 | 0 | 0 | 0/3 |
| foxtail | 7/2 | 0/2 | 0 | 8/2 |
| Johnsongrass | 0 | 0 | 0 | 0 |
| wild oats | 7/2 | 0 | 0 | 5/2 |

Example XXII

The compounds of Examples I and II were applied as post-emergence herbicides according to the procedure of Example XXI at rates of 0.25 and 0.75 pound per acre. The results are given in Table III.

TABLE III

| Plant Species | Activity - Post | | | |
|---|---|---|---|---|
| | Cmpd. I (lb./A.) 0.25 | Cmpd. I (lb./A.) 0.75 | Cmpd. II (lb./A.) 0.25 | Cmpd. II (lb./A.) 0.75 |
| alfalfa | 9 | 9 | 9 | 9 |
| corn | 0 | 0/1 | 0 | 0/1 |
| cotton | 8/3 | 9 | 9 | 8/2 |
| dry beans | 7/4 | 9 | 8/4 | 8/4 |
| peanuts | — | — | 0/1 | 0/1 |
| rice | 0/1 | 0/2 | 0/1 | 0/1 |
| soybeans | 0/2 | 6/4 | 0/4 | 0/3 |
| wheat | 0 | 0/2 | 0 | 0/1 |
| cocklebur | 7/2 | 8/3 | 7/3 | 8/2 |
| jimsonweed | 8/4 | 9 | 9 | 9 |
| lambsquarters | 8/4 | 9 | 9 | 9 |
| morningglory | 0 | 5/4 | 0/3 | 7/4 |
| mustard | 8/3 | 9 | 9 | 9 |
| prickly sida | 8/3 | 9 | 7/3 | 9 |
| pigweed | 8/3 | 9 | 9 | 9 |
| sesbania | 5/4 | 8/4 | 5/3 | 9 |
| velvetleaf | 9 | 9 | 9 | 9 |
| barnyardgrass | 0 | 0/2 | 0 | 0 |
| foxtail | 0 | 8/2 | 5/2 | 9 |
| Johnsongrass | 0 | 0/1 | 0 | 0 |
| wild oats | 0/3 | 7/2 | 0 | 6/3 |

Example XXIII

Compounds I, II and X were also evaluated as pre-emergence herbicides against the same broad group of crops and weeds at 1 and 2 pounds per acre. The greenhouse flats were planted and then on the same day sprayed with an ethanol solution of the compound. Evaluations were made twenty-one days after treatment as described in Example XXI. The results are given in Table IV.

TABLE IV

| Plant Species | Activity - Pre | | | | | |
|---|---|---|---|---|---|---|
| | Cmpd. I (lb./A.) 1 | Cmpd. I (lb./A.) 2 | Cmpd. II (lb./A.) 1 | Cmpd. II (lb./A.) 2 | Cmpd. X (lb./A.) 1 | Cmpd. X (lb./A.) 2 |
| alfalfa | 9 | 9 | 6/3 | 9 | 6/0 | 9 |
| corn | 0 | 0/1 | 0 | 0 | 0 | 0 |
| cotton | 0 | 0/2 | 0/1 | 0/1 | 0/1 | 0/1 |
| dry beans | 0 | 0/3 | 0/2 | 5/4 | 0/1 | 6/2 |
| peanuts | 0/1 | 0 | 0 | 0 | 0 | 0 |
| rice | 0 | 0 | 0 | 0 | 0/1 | 5/1 |
| soybeans | 0/1 | 5/3 | 0/1 | 6/3 | 0/1 | 0/1 |
| wheat | 0 | 0 | 0 | 0/1 | 0 | 0 |
| cocklebur | 0 | 0 | 0 | 0/1 | 0 | 0/1 |
| jimsonweed | 8/3 | 8/4 | 0/1 | 6/2 | 8/3 | 8/4 |
| lambsquarters | 7/3 | 8/4 | 5/2 | 8/3 | — | — |
| morningglory | 0/1 | 0/2 | 0 | 0/1 | 0 | 0/1 |
| mustard | 8/4 | 9 | 9 | 9 | 8/1 | 8/4 |
| prickly sida | 5/3 | 8/4 | 0/2 | 5/3 | 5/2 | 8/2 |
| pigweed | 8/4 | 9 | 8/3 | 9 | 7/3 | 8/4 |
| sesbania | 5/2 | 7/2 | 0/1 | 0/1 | 0 | 5/1 |

TABLE IV-continued

| | Activity - Pre | | | | | |
|---|---|---|---|---|---|---|
| Plant | Cmpd. I (lb./A.) | | Cmpd. II (lb./A.) | | Cmpd. X (lb./A.) | |
| Species | 1 | 2 | 1 | 2 | 1 | 2 |
| velvetleaf | 9 | 9 | 6/2 | 9 | 7/1 | 8/2 |
| barnyardgrass | 0/2 | 5/3 | 0/1 | 5/2 | 5/1 | 9 |
| foxtail | 5/3 | 8/4 | 5/2 | 5/3 | 8/2 | 9 |
| Johnsongrass | 0 | 0/2 | 0 | 0 | 0/2 | 5/2 |
| wild oats | 0 | 5/2 | 0 | 0 | 0 | 5/1 |
| ragweed | — | — | — | — | 6/2 | 9 |
| nightshade | — | — | — | — | 8/4 | 8/4 |

Example XXIV

Compound II was tested at 1 and 2 pounds per acre as a pre-emergence treatment with soil incorporation. The procedure of Example XXIII was repeated except the chemical was incorporated by mixing it into the top one inch of soil prior to planting the seeds. The results are given in Table V.

TABLE V

| Plant | Activity - Pre-Incorporated Cmpd. II (lb./A.) | |
|---|---|---|
| Species | 1 | 2 |
| alfalfa | 9 | 9 |
| corn | 0/1 | 0/1 |
| cotton | 0 | 0 |
| dry beans | 0/3 | 0/3 |
| peanuts | 0/1 | 0/1 |
| rice | 0/2 | 0/3 |
| soybeans | 0/2 | 0/3 |
| wheat | 0/1 | 0/3 |
| cocklebur | 0/1 | 0/2 |
| jimsonweed | 8/4 | 8/4 |
| lambsquarters | 6/2 | 5/2 |
| morningglory | 5/3 | 8/4 |
| mustard | 8/4 | 9 |
| prickly sida | 8/4 | 9 |
| pigweed | 8/4 | 8/4 |
| sesbania | 5/2 | 7/2 |
| velvetleaf | 8/4 | 9 |
| barnyardgrass | 5/3 | 8/4 |
| foxtail | 7/4 | 8/4 |
| Johnsongrass | 0/2 | 5/3 |
| wild oats | 0/2 | 6/3 |

Since a relatively small amount of one or more of the active compounds should be uniformly distributed over the area to be treated, they preferably are formulated with conventional herbicide carriers, either liquid or solid. Thus, the compounds can be impregnated on or admixed with a pulverulent solid carrier such as lime, talc, clay, Bentonite, calcium chloride, vermiculite and the like. Alternatively, they can be dissolved or suspended in a liquid carrier such as water, kerosene, alcohols, diesel oil, mineral oil, xylene, benzene, glycols, ketones, and the like. Since the compounds will form water-soluble salts such as with mineral acids, they can be readily formulated with water.

A surfactant is preferably included to aid in dispersion, emulsification and coverage. The surfactant can be ionic or nonionic and may be liquid or solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

Various changes and modifications of the invention can be made, and, to the extent that such variations incorporate the spirit of this invention, they are intended to be included within the scope of the appended claims.

What is claimed is:

1. A compound of the formula

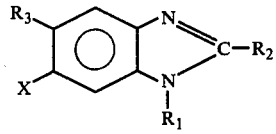

in which $R_1$ and $R_2$ are each alkyl of 1 to 3 carbon atoms, $R_3$ is a branched chain alkyl group of 3 to about 6 carbon atoms, and X is hydrogen or halogen, and the phytotoxic salts thereof.

2. A compound according to claim 1 in which X is bromo or chloro.

3. A compound according to claim 1 in which $R_1$ and $R_2$ are methyl.

4. A compound according to claim 1 in which X is hydrogen and $R_3$ is isopropyl.

5. A compound according to claim 1 in which X is hydrogen and $R_3$ is tert-butyl.

6. A compound according to claim 1 in which said phytotoxic salt is the hydrogen chloride salt.

7. The compound according to claim 1, 1,2-dimethyl-5-isopropylbenzimidazole.

8. The compound according to claim 1, 1,2-dimethyl-5-tert-butylbenzimidazole.

9. A herbicidal composition comprising a phytotoxic amount of a compound of claim 1, a surfactant, and an inert carrier therefor.

10. The method of controlling weed growth which comprises applying a phytotoxic amount of a compound of claim 1 to the locus of said weed growth.

11. The method according to claim 10 in which $R_1$ and $R_2$ are methyl.

12. The method according to claim 10 in which X is hydrogen and $R_3$ is selected from isopropyl and tert-butyl.

13. The method according to claim 10 in which said compound is 1,2-dimethyl-5-isopropylbenzimidazole.

14. The method according to claim 10 in which said compound is 1,2-dimethyl-5-tert-butylbenzimidazole.

* * * * *